United States Patent [19]
Stepan

[11] Patent Number: 6,036,312
[45] Date of Patent: *Mar. 14, 2000

[54] PROTECTIVE EYEGLASS ASSEMBLY HAVING A UNITARY, DECENTERED LENS PIECE

[75] Inventor: Walter Stepan, Lincoln, R.I.

[73] Assignee: Bacou USA Safety, Inc., Smithfield, R.I.

[*] Notice: This patent is subject to a terminal disclaimer.

[21] Appl. No.: 08/957,478

[22] Filed: Oct. 24, 1997

[51] Int. Cl.⁷ .............................. G02C 7/02; G02C 1/04; G02C 5/14

[52] U.S. Cl. .......................... 351/159; 351/41; 351/106; 351/116

[58] Field of Search ............................... 351/159, 41, 47, 351/103–104, 105–106, 86, 116

[56] References Cited

U.S. PATENT DOCUMENTS

| | | | |
|---|---|---|---|
| 5,000,558 | 3/1991 | Blackstone | 351/41 |
| 5,208,614 | 5/1993 | Jannard | 351/159 |
| 5,530,490 | 6/1996 | Canavan | 351/106 |
| 5,614,964 | 3/1997 | Garneau | 351/41 |
| 5,648,832 | 7/1997 | Houston et al. | 351/159 |
| 5,796,461 | 8/1998 | Stepan | 351/106 |
| 5,825,455 | 10/1998 | Fecteau et al. | 351/159 |
| 5,907,868 | 6/1999 | Schleger et al. | 351/47 |

*Primary Examiner*—Georgia Epps
*Assistant Examiner*—Jordan M. Schwartz
*Attorney, Agent, or Firm*—Salter & Michaelson

[57] ABSTRACT

A protective eyeglass assembly includes a unitary, decentered lens piece integrally molded from a transparent plastic material. The lens piece includes left and right lens panels connected by a central bridge portion. The left and right lens panels each have a lens body with a front surface and a rear surface, the front and rear surfaces defining a lens thickness therebetween. The front surface conforms substantially to a portion of the surface of a sphere having a first center whereas the rear surface conforms substantially to a portion of the surface of a sphere having a second center. The first center and the second center are offset from one another to taper the lens thickness. A frame supports the lens piece on a wearer. Alternatively, temple bars can be hingedly mounted directly onto the lens piece for supporting lens piece on the wearer.

16 Claims, 5 Drawing Sheets

PROTECTIVE EYEGLASS ASSEMBLY HAVING A UNITARY, DECENTERED LENS PIECE

BACKGROUND OF THE INVENTION

The instant invention relates to protective eyewear, and more particularly to a protective eyeglass assembly including a unitary, decentered lens piece which can be readily assembled and disassembled with a frame or a pair of temple bars for quick and efficient interchange of the frame and/or replacement of the lens piece, and which reduces optical distortion.

The importance of wearing safety or protective glasses in many industrial environments is widely recognized, and as a result, a variety of different types and styles of protective eyeglasses have been heretofore available. While the currently existing protective eyeglasses are adequate for their intended purpose, there is nevertheless a continuing need for improved versions of protective eyeglasses. In this regard, protective eyeglasses which mimic current designer frame styles and which offer versatility to change frame colors or styles, and to replace lens pieces are believed to be highly desirable in the market.

An example of one type of protective eyeglass assembly can be found in applicant's co-pending patent application, Ser. No. 08/635,204, entitled PROTECTIVE EYEGLASS ASSEMBLY. This patent application discloses a protective eyeglass assembly comprising a frame, and a lens piece which is adapted to be detachably secured to the frame so that a user can interchange the frame for another frame of the same type, but of a different color or appearance, and/or replace the lens piece if the lens piece becomes damaged. The frame comprises left and right lens frame portions, left and right lens receiving apertures respectively formed in the left and right lens frame portions, a bridge portion connecting the left and right lens frame portions, and left and right temple bars extending rearwardly from the left and right lens frame portions. Preferably, the temple bars are angularly adjustable with respect to the left and right lens frame portions, and are also telescopically adjustable in length.

The lens piece is preferably integrally molded from a durable, transparent, plastic material and includes left and right lens panels, a central bridge portion connecting the left and right lens panels, left and right side shields extending rearwardly from left and right side extremities of the left and right lens panels, and left and right upper shields extending between left and right upper extremity portions of the left and right lens panels, and the left and right side shields, respectively. The left and right lens panels, left and right side shields, and left and right upper shields each have a uniform thickness.

The lens piece is received in assembled relation with the frame with the left and right lens panels aligned in registry with the left and right lens frame portions. The lens piece and the frame are secured in assembled relation by means of interengaging formations on the frame and lens piece. More specifically, the left and right temple bars each include an inwardly extending, horizontally disposed T-shaped pin, while the left and right side shields of the lens piece include a complementary vertically disposed slot for receiving their respective pins. The central bridge portion of the lens piece further includes a detent, while the bridge portion of the frame includes a small recess for receiving the detent. To assemble the frame and lens piece, the temple bars of the frame are bent outwardly to insert the pins into the slots in the side shields of the lens piece. In this regard, the lens piece is originally positioned with the lens panels facing downwardly so that the slots in the side shields are disposed horizontally and aligned with the pins, and then the lens piece is rotated forwardly and upwardly with respect to the frame to engage the lens piece detent with the recess in the bridge portion of the frame. The pins along with the detent cooperate to maintain the lens piece in assembled relation with the frame.

It has been found that the protective eyeglass assembly as disclosed in the aforementioned patent application has significant marketing advantages over existing protective eyeglasses. Specifically, because the lens piece is removable from the frame, the frame can be interchanged with another frame of a different color or appearance by simply disassembling the lens piece from the original frame and assembling it with a new frame. Furthermore, the particular design of the frame and lens piece is intended to minimize the visibility of the lens piece, and thereby create the perception of a conventional pair of designer glasses rather than a bulky pair of protective goggles. The provision of designer style protective eyewear makes it more fashionable to wear the protective eyewear, and thus increases the number of people who will actually wear protective eyewear. Still further, because of the unitized construction of the lens piece and the manner in which it is adapted for assembly with the frame, the lens piece is able to provide highly effective eye protection. Even further still, the overall construction of the frame and lens piece enables the protective eyeglasses of the subject invention to be comfortably and effectively worn by a user for a prolonged period of time.

Although perfectly suitable for its intended purpose, the eyeglass assembly disclosed in the aforementioned patent application does suffer from the disadvantage of distorting the wearer's vision. Specifically, the uniform thickness of the left and right lens panels incur a nominal amount of prismatic distortion. The present invention overcomes this disadvantage by providing a unitary, decentered lens piece which is tapered to significantly reduce such distortion.

SUMMARY OF THE INVENTION

The instant invention provides a novel and effective protective eyeglass assembly which comprises a unitary, decentered lens piece integrally molded from a transparent plastic material. The lens piece includes left and right lens panels connected by a central bridge portion. The left and right lens panels each have a lens body with a front surface and a rear surface, the front and rear surfaces defining a lens thickness therebetween. The front surface conforms substantially to a portion of the surface of a sphere having a first center whereas the rear surface conforms substantially to a portion of the surface of a sphere having a second center. The first center and the second center are offset from one another to taper the lens thickness. Support means supports the lens piece on a wearer.

More specifically, the lens piece further includes left and right side shields extending rearwardly from respective left and right side extremities of the left and right lens panels, and left and right upper shields extending between left and right upper extremity portions of the left and right lens panels and the left and right side shields, respectively. The left and right lens panels are positioned with respect to one another such that an optical centerline drawn through the first and second centers is spaced from and maintained substantially parallel with the wearer's normal line of sight in each of a horizontal plane and vertical plane.

In one embodiment, the support means comprises a frame including left and right lens frame portions connected by a central bridge portion, the left and right lens frame portions each having a lens receiving aperture. The frame further includes left and right temple bars. The arrangement is such that the lens piece is received in assembled relation with the frame with the left and right lens panels aligned in registry with the left and right lens frame portions.

In another embodiment, the support means comprises left and right temple bars hingedly secured to the left and right side shields of the lens piece.

Accordingly, the primary object of the instant invention is the provision of a protective eyeglass assembly comprising a lens piece and a frame and/or a pair of temple bars which is (are) detachable from the lens piece for interchanging the frame with another frame of a different color or appearance, and/or replacement of the lens portion if the lens portion becomes scratched or damaged. Another primary object is the provision of a lens piece having lens panels which significantly reduce optical distortion when worn.

Further additional objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention.

Corresponding reference numerals designate corresponding parts throughout the several views of the drawings.

DETAILED DESCRIPTION OF THE PREFERRED EMBODIMENTS

Figure 1:
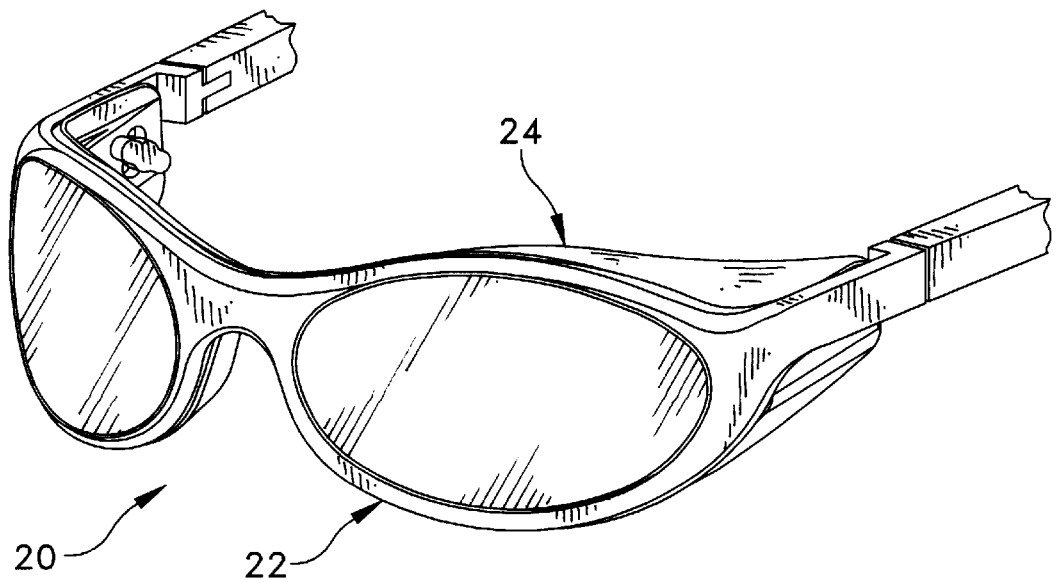
FIG. 1 is a perspective view of the eyeglass assembly of the instant invention.

Referring now to the drawings, the protective eyeglass assembly of the instant invention is illustrated and generally indicated at 20 in FIG. 1. The eyeglass assembly 20 comprises a frame, generally indicated at 22, and a lens piece, generally indicated at 24, which is removably secured to the frame 22 as will hereinafter be more fully set forth.

Referring particularly to FIGS. 2–5, the lens piece 24 is preferably integrally molded from a durable, transparent plastic material, and includes left and right lens panels, generally indicated at 26, 28, a central bridge portion 30 connecting the left and right lens panels 26, 28, left and right side shields 32, 34 extending rearwardly from left and right side extremities 43a, 43b of the left and right lens panels 26, 28, and left and right upper shields 36, 38 extending between left and right upper extremity portions 45a, 45b of the left and right lens panels 26, 28 and the left and right side shields 32, 34, respectively.

Each lens panel 26, 28 is constructed generally in accordance with the teachings provided in U.S. Pat. No. 5,648, 832 to Houston et al., which is incorporated herein by reference. Specifically, each lens panel 26, 28 extends from a medial edge 40 (FIGS. 3 and 4) throughout at least a portion and preferably substantially all of the wearer's range of vision to a lateral edge 42. The arc length of each lens panel 26, 28 from the medial edge 40 to the lateral edge 42 will generally be within the range from about 40 mm to about 90 mm, and is preferably about 60 mm.

Figure 4:
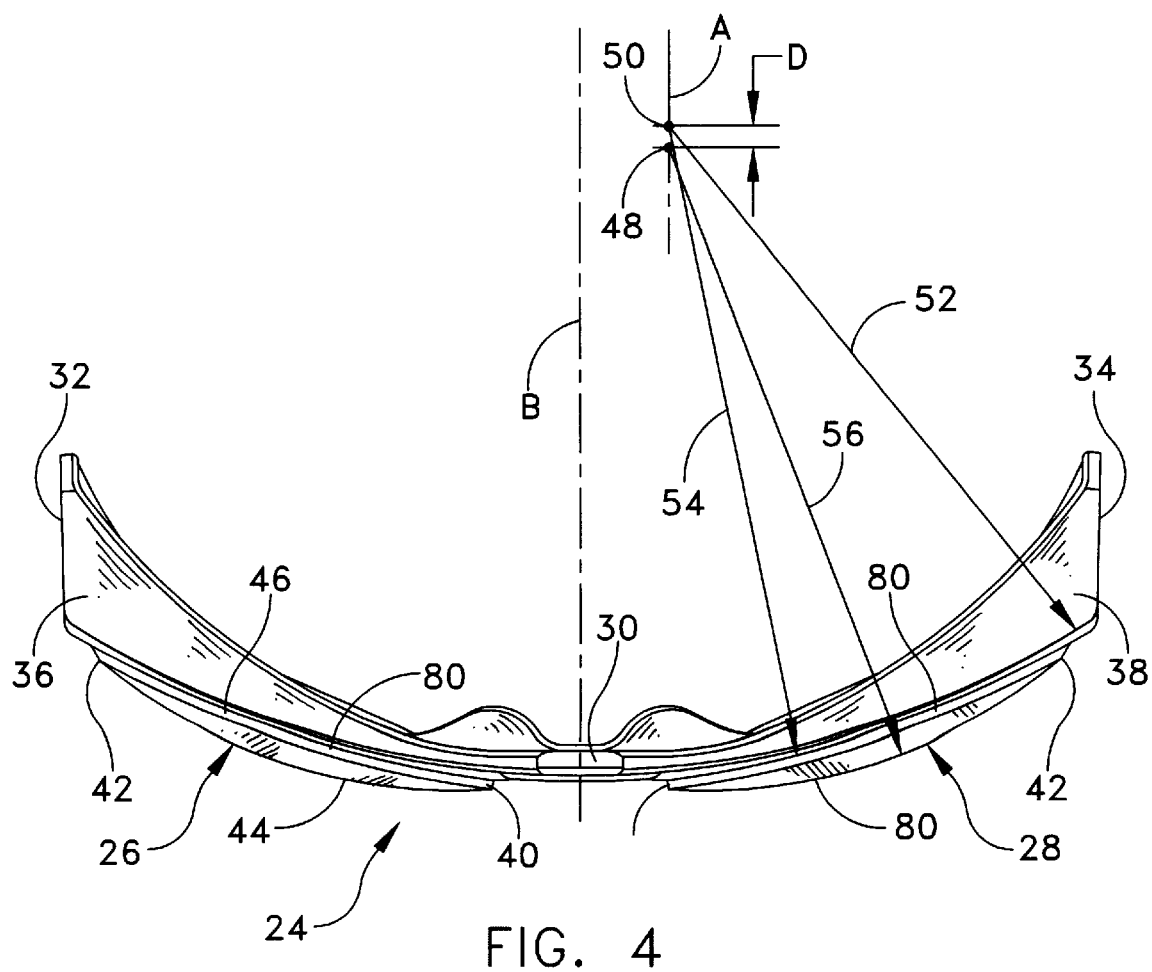
FIG. 4 is a top plan view of the lens piece.
Figure 5:
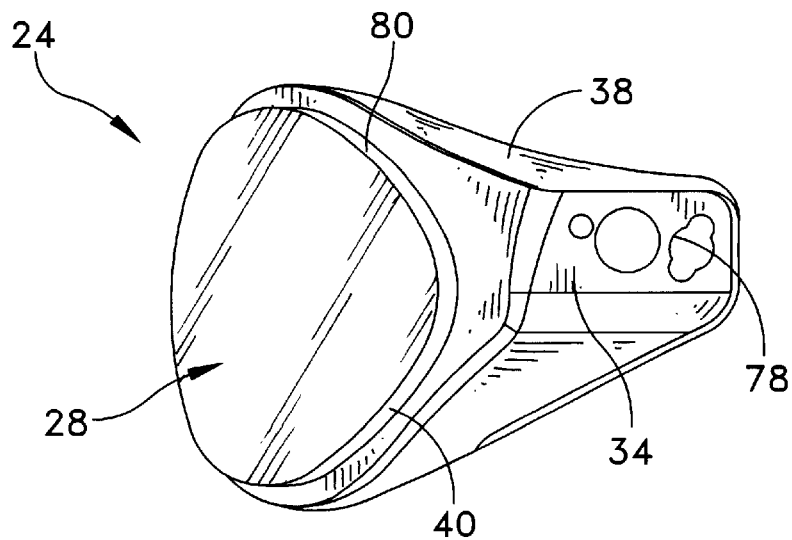
FIG. 5 is a side elevational view of the lens piece.
Figure 6:
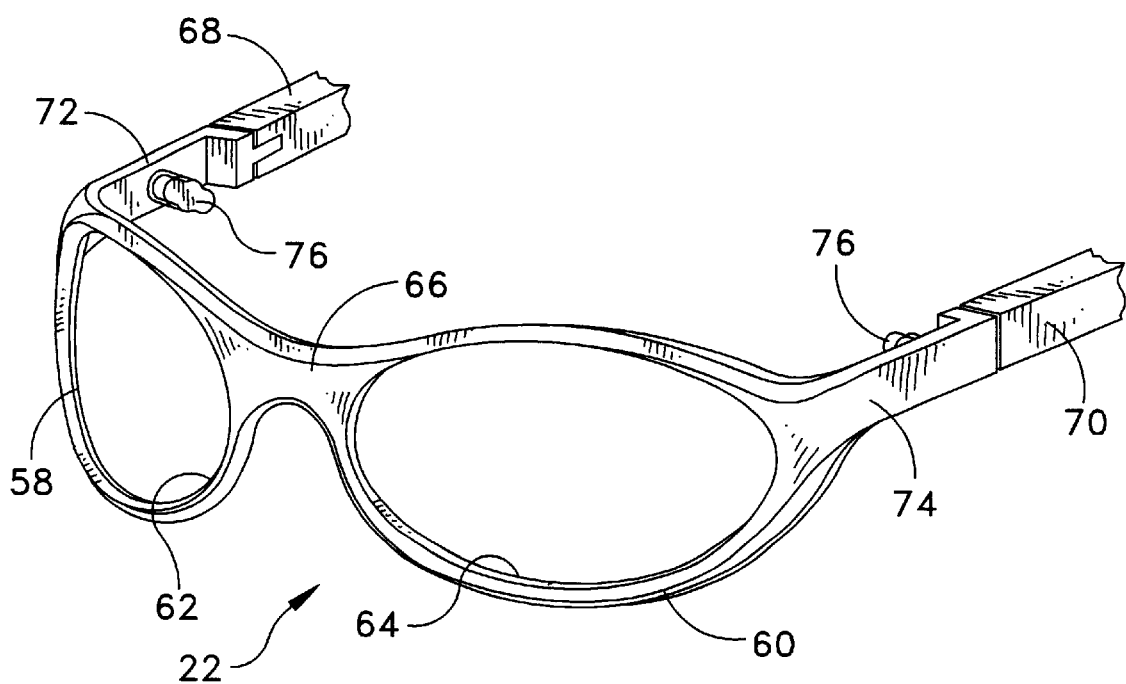
FIG. 6 is a perspective view of a frame of the eyeglass assembly.
Figure 7:
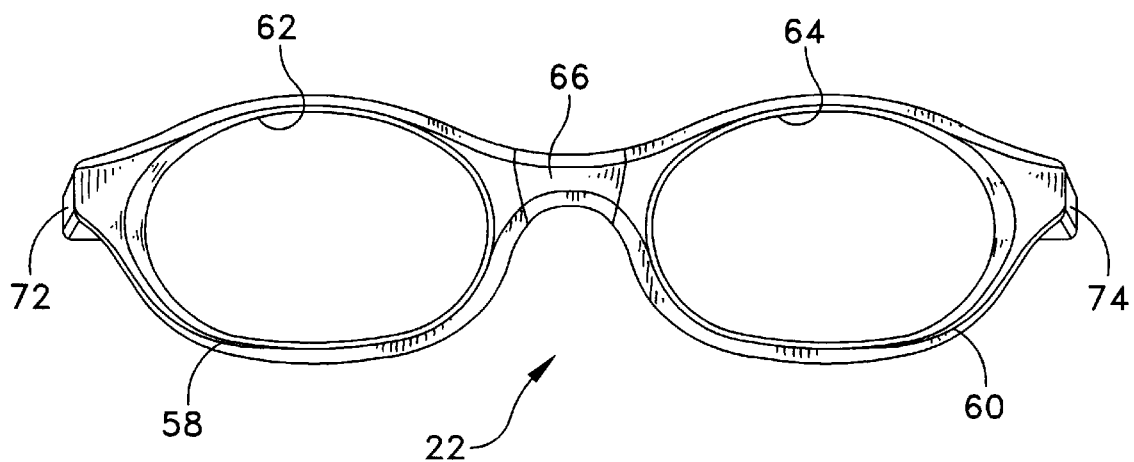
FIG. 7 is a front elevational view of the frame.
Figure 8:
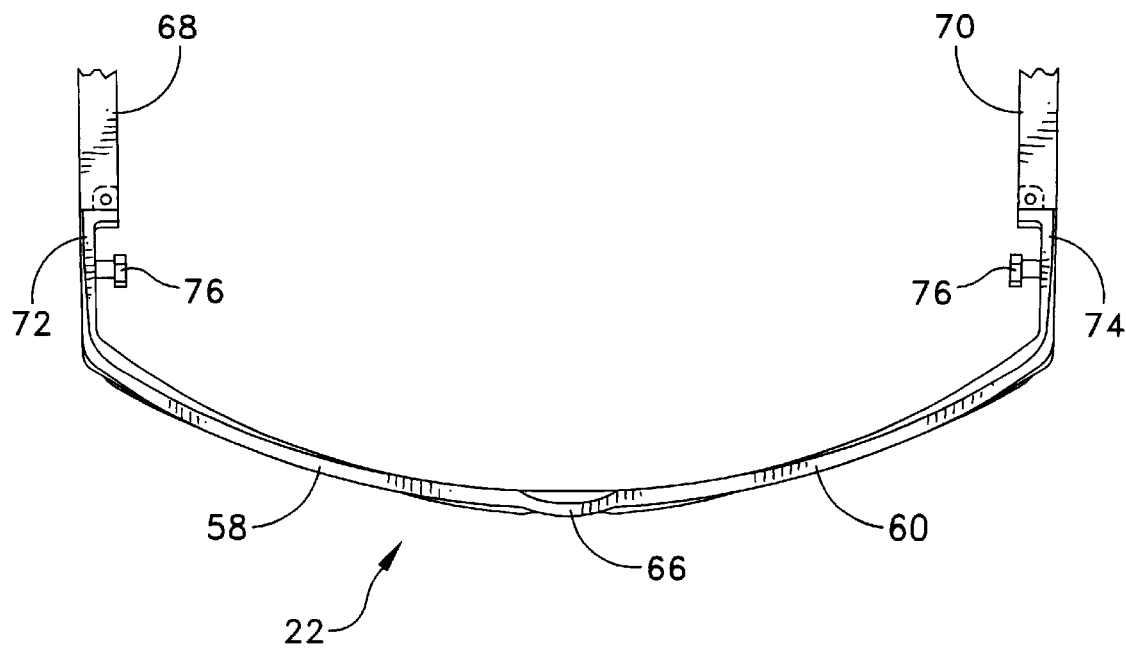
FIG. 8 is a top plan view of the frame.
Figure 9:
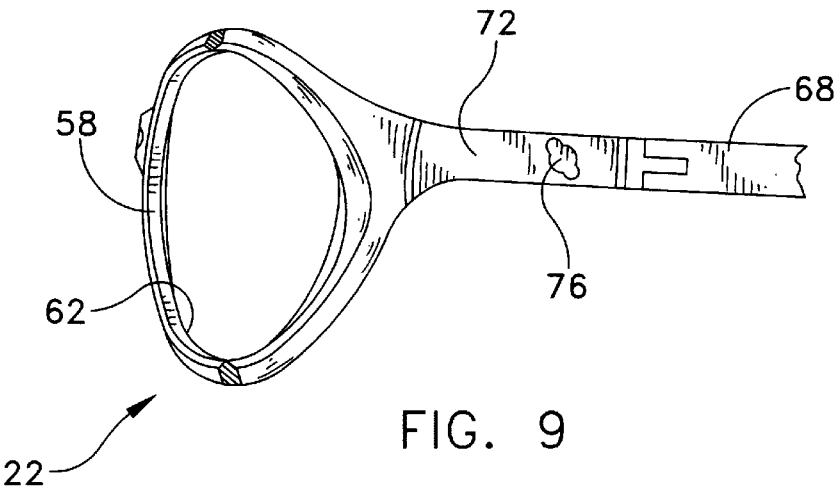
FIG. 9 is a side elevational view of the interior of the frame.

Each lens panel 26, 28 is further provided with a lens body having a front surface 44 and a rear surface 46, and a varying thickness therebetween (see FIG. 4). When worn, each lens panel 26, 28 extends across the wearer's normal line of sight, and preferably substantially across the wearer's peripheral zones of vision. The thickness of each lens panel 26, 28 tapers smoothly from the maximum thickness proximate to the medial edge 40 to a relatively lesser thickness at the lateral edge 42.

As shown in FIG. 4, the front and rear surfaces 44, 46 of each lens panel 26, 28 conform to offset circles represented by center points 48, 50, respectively. A line drawn through the center points 48, 50, referred to herein as the optical centerline A of the lens panel (e.g., lens panel 28 in FIG. 4), is collinear with the normal line of sight and parallel to a centerline B extending through the bridge portion 30. Preferably, the center points 48, 50 are offset from one another a distance D which, in the shown embodiment, is approximately 1.60 mm along the optical centerline A.

The front surface 44 of each lens panel 26, 28 generally conforms to a portion of the surface of a regular geometric solid, such as a sphere, the radius of which is represented by reference numeral 52. For example, in the shown embodiment, the radius of the sphere 52 is preferably 66.25 mm. Similarly, the rear surface 46 of each lens panel 26, 28 generally conforms to a portion of the surface of a sphere, the radius of which is represented by reference numeral 54 and is preferably 65.26 mm. The radius of the rear surface 46 at the junction of the lens panel 26, 28 and its respective side shield 32, 34 is approximately 66.45 mm, and is represented by reference numeral 56.

It should be understood that the construction of each lens panel 26, 28, and the rationale for its construction can be generally obtained from the Houston et al. patent. Thus, no further explanation of the detailed construction of the lens panels 26, 28 is necessary.

Turning to FIGS. 6–9, the frame 22 is preferably constructed from a durable plastic material, and comprises left and right lens frame portions 58, 60, respectively, left and right lens receiving apertures 62, 64, respectively formed in the left and right lens frame portions 58, 60, a central bridge portion 66 connecting the left and right lens frame portions 58, 60, and left and right temple bars 68, 70 extending rearwardly from the left and right lens frame portions 58, 60. More specifically, the left and right lens frame portions 58, 60 include respective side bar portions 72, 74 which extend rearwardly from the peripheral edges of the respective lens frame portions 58, 60, and the temple bars 68, 70 are attached to these side bar portions 72, 74 of the frame 22. As shown, the temple bars 68, 70 are hinged in the well known manner for folding inwardly to a compact configuration.

It should be noted that the temple bars 68, 70 can be angularly adjustable with respect to the left and right lens frame portions 58, 60 by means of a ratchet assembly, but are not illustrated in this manner. In addition, the temple bars 68, 70 can further be telescopically adjustable in length as is known in the art.

The lens piece 24 is received in assembled relation with the frame 22, with the left and right lens panels 26, 28 aligned in registry with the left and right lens frame portions 58, 60. More specifically, the lens piece 24 and the frame 22 are detachably secured in assembled relation by means of interengaging formations on the frame 22 and lens piece 24. Still more specifically, the left and right side bars 72, 74 of the frame 22 each include an inwardly projecting, horizontally disposed, T-shaped pin 76 (seen most clearly in FIGS. 8 and 9), while the left and right side shields 32, 34 of the lens piece 24 each include a complementary slot 78 for receiving the respective pin 76. Although not shown, the central bridge portion 30 of the lens piece 24 can further include a detent, while the bridge portion 66 of the frame 22 includes a small recess (not shown) for receiving the detent.

To assemble the lens piece 24 and the frame 22, the temple bars 68, 70 of the frame 22 are bent outwardly to insert the T-shaped pins 76 into the slots 78 in the side shields 32, 34 of the lens piece 24. In this regard, the lens piece 24 is first positioned with the lens panels 26, 28 facing downwardly so that the slots 78 are oriented horizontally and aligned with the uniquely-shaped pins 76. The lens piece 24 is then rotated upwardly and forwardly with respect to the frame 22 to interlock the pins 76 with the slots 78, and to engage the lens piece detent with the recess in the bridge portion 66 of the frame 22, if provided.

Referring back to FIG. 3, it is pointed out that the left and right lens panels 26, 28 and the bridge portion 30 of the lens piece 24 are preferably formed with an outer peripheral margin which is generally similar to the outer peripheral margin of the left and right lens frame portions 58, 60 and the bridge portion 66 of the frame 22 such that the lens piece 24 is substantially hidden from view when viewing the eyeglass assembly 20 from a frontal viewing position (not shown). The intention of this arrangement is to create the perception that the wearer is not actually wearing protective glasses, rather that they are wearing a conventional pair of glasses.

Figure 2:
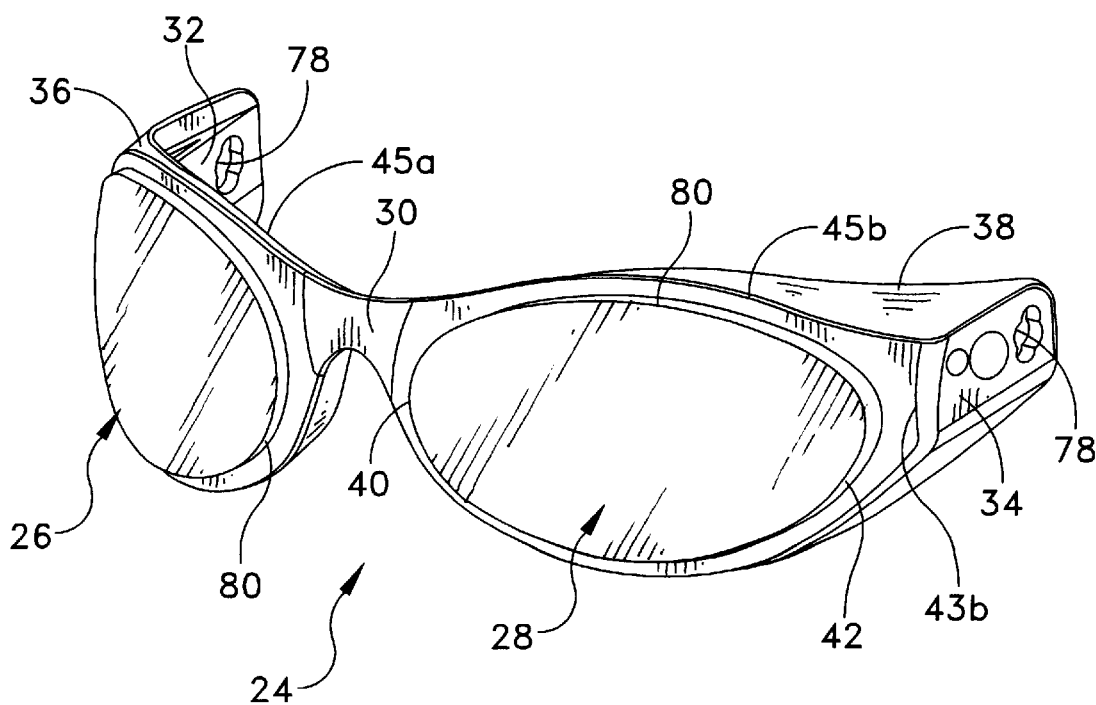
FIG. 2 is a perspective view of a lens piece of the eyeglass assembly illustrated in FIG. 1.
Figure 3:
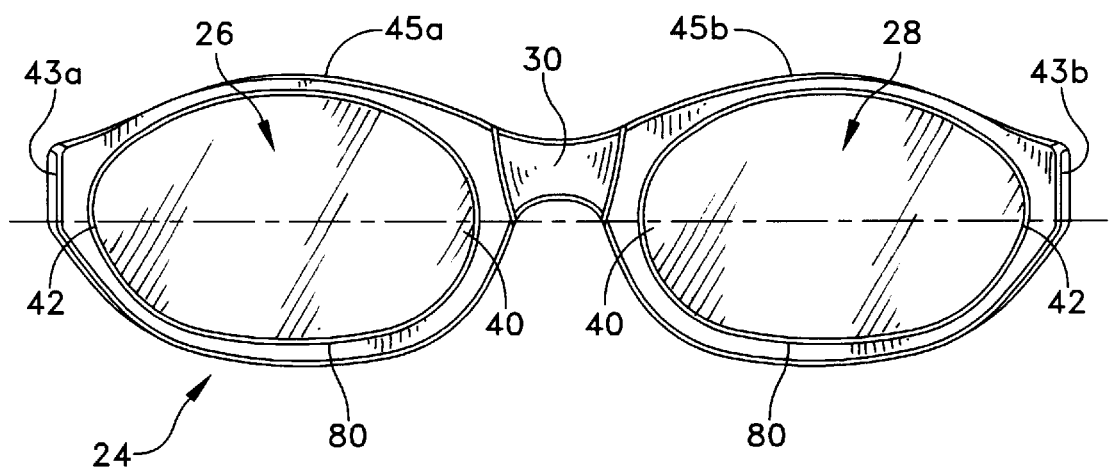
FIG. 3 is a front elevational view of the lens piece.

Referring to FIGS. 2 and 3, the left and right lens panels 26, 28 each further comprise a stepped lens formation 80 which is received in interfitting engagement into its respective aligned lens receiving aperture 62, 64 of the frame 22 when the lens piece 24 is assembled with the frame 22. The stepped formations 80 have an outer peripheral margin which is substantially identical to the outer peripheral margin of the lens apertures 62, 64 such that the stepped formations 80 appear as inserted lenses when the lens piece 24 is assembled with the frame 22. The outer peripheral sides of the stepped formations 80 and the inner peripheral sides of the lens apertures 62, 64 further include complementary chamfered edges, respectively, for a snug interfitting engagement of the lens piece 24 and the frame 22.

Figure 10:
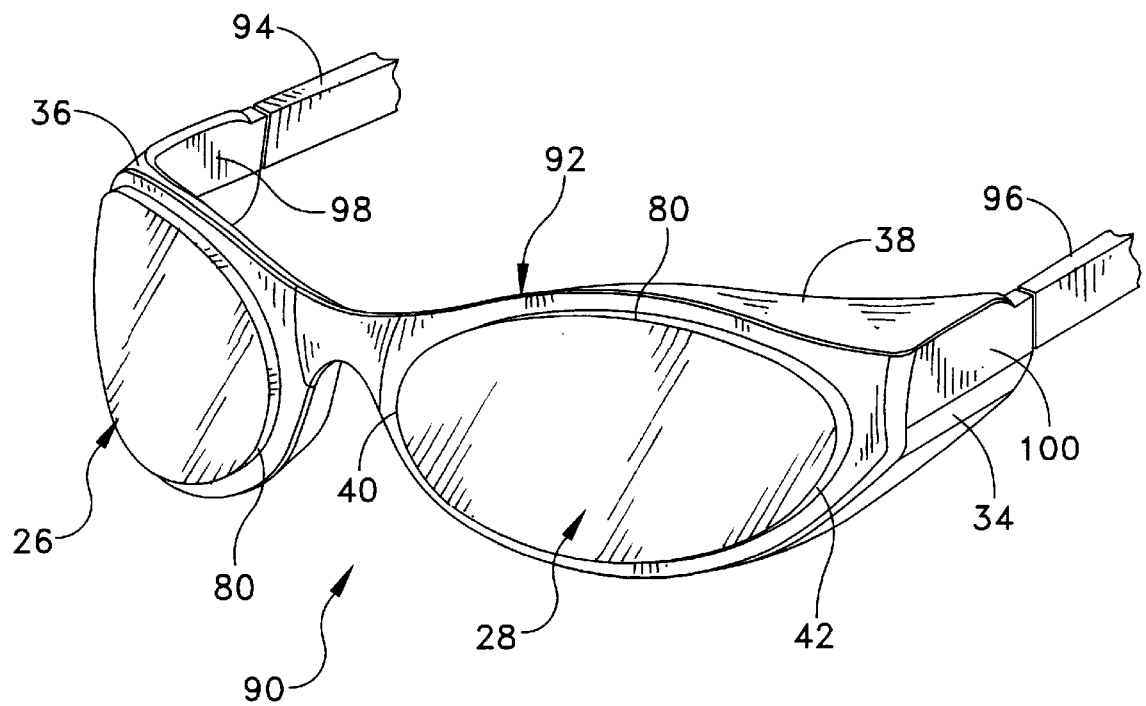
FIG. 10 is a perspective view of a eyeglass assembly of another preferred embodiment having temple bars directly mounted on a lens piece of the eyeglass assembly.

FIG. 10 illustrates a protective eyeglass assembly, generally indicated at 90, of another preferred embodiment. As shown, eyeglass assembly 90 includes a lens piece, generally indicated at 92, constructed nearly identically as lens piece 24 wherein parts designated herein will be correspondingly referenced. Temple bars 94, 96 are hingedly mounted on respective left and right shield portions 32, 34 of the lens piece 92 by a pair of U-shaped clips 98, 100; however, it should be understood that any suitable means can be provided to achieve the attachment of the temple bars 94, 96 to the side shield portions 32, 34. Thus, it should be noted that with eyeglass assembly 90, the frame is not necessary since the lens piece 92 serves as the support structure for mounting the temple bars 94, 96 thereon.

It is seen, therefore that the instant invention provides an effective protective eyeglass assembly which has significant advantages over the heretofore available safety eyeglasses. Specifically, because the lens piece is formed as one piece and each lens panel is tapered in the manner set forth above, optical distortion of the wearer is avoided.

Also, since the lens piece is removable from the frame, the frame can be interchanged with another frame of a different color or appearance by simply disassembling the lens piece from the original frame and assembling it with a new frame. Furthermore, the particular design of the frame and lens piece is intended to minimize the visibility of the lens piece, and thereby create the perception of a conventional pair of designer glasses. The provision of designer style protective eyewear makes it more fashionable to wear the protective eyewear, and thus increases the number of people who will actually wear protective eyewear. Still further, because of the unitized construction of the lens piece and the manner in which it is adapted for assembly with the frame, the lens piece is able to provide highly effective eye protection. Even further still, the overall construction of the frame and lens piece enables the protective eyeglasses of the subject invention to be comfortably and effectively worn by a user for a prolonged period of time. Yet further, the stepped lens formations of the lens piece create he perception of inserted lenses within the frame. Also, the temple bars can be mounted directly on the lens piece to obviate the need of the frame.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A protective eyeglass assembly comprising:
a unitary, decentered lens piece integrally molded from a transparent plastic material, said lens piece including;
(a) left and right lens panels each including a medial edge and a lateral edge, and each further having a lens body with a front surface and a rear surface, the front and rear surfaces defining a lens thickness therebetween, the front surface conforming substantially to a portion of the surface of a sphere having a first center, the rear surface conforming substantially to a portion of the surface of a sphere having a second center being offset from one another to taper the lens thickness, (b) a central bridge portion connecting said left and right panels and (c) a left side shield and a right side shield extending rearwardly from respective left and right side extremities of said left and right lens panels, said left and right side shields being constructed and arranged to provide protection against peripheral injury to a wearer's eyes;
a support member constructed and arranged to support the lens piece on the wearer and including a left and a right temple bar extending rearwardly from side edges of said left and right side shields and supported by said left and right side shields; and
wherein the unitary, decentered lens piece is readily removable from the support member such that the lens piece may be easily interchanged with other unitary lens pieces by the wearer.

2. The eyeglass assembly of claim 1, said lens piece further including left and right upper shields extending between left and right upper extremity portions of said left and right lens panels and said left and right side shields, respectively.

3. The eyeglass assembly of claim 2, said support member further comprising a frame including left and right lens frame portions connected by a central bridge portion, said left and right lens frame portions each including a lens receiving aperture, said lens piece being received in assembled relation with said frame with said left and right lens panels aligned in registry with said left and right lens frame portions.

4. The eyeglass assembly of claim 3, said left and right lens panels and said bridge portion of said lens piece having an outer peripheral margin which is generally similar to an outer peripheral margin of said left and right frame portion and said bridge portion of said frame such that said lens piece, excluding substantially all of the left and right lens panels, is substantially hidden from view when viewing said eyeglass assembly from a frontal viewing position.

5. The eyeglass assembly of claim 3, said left and right lens panels each including a stepped lens formation, said stepped lens formation being respectively received in interfitting engagement in the lens receiving aperture of the frame portions of the frame when said lens piece is assembled with said frame.

6. The eyeglass assembly of claim 5, the outer peripheral margins of said stepped lens formations being substantially identical to the inner peripheral margins of the respective lens receiving apertures.

7. The eyeglass assembly of claim 3 further comprising means for detachably securing said lens piece to said frame when said lens piece is received in assembled relation with said frame.

8. The eyeglass assembly of claim 7, said means for detachably securing said lens piece to said frame including means for detachably securing said left and right temple bars to said left and right side shields of said lens piece.

9. The eyeglass assembly of claim 1, said left and right temple bars being hingedly secured to the left and right side shields of said lens piece by a pair of clip members.

10. The eyeglass assembly of claim 2, said left and right lens panels being positioned with respect to one another such that an optical centerline drawn through the first and second centers is spaced from and maintained substantially parallel with the wearer's normal line of sight in each of a horizontal plane and vertical plane.

11. The eyeglass assembly of claim 1, said left and right lens panels being positioned with respect to one another such that an optical centerline drawn through the first and second centers is spaced from and maintained substantially parallel with the wearer's normal line of sight in each of a horizontal plane and vertical plane.

12. The eyeglass assembly of claim 1, wherein the left and right side shields each include a slot disposed therein for receiving a corresponding left and right pin extending from respective left and right side bars which are connected to a left and right temple bar, respectively, so as to support the left and right temple bars on said respective left and right side shields.

13. The eyeglass assembly of claim 8, wherein said means for detachably securing said left and right temple bars to said left and right side shields of said lens piece includes a left and a right side bar connected to said respective left and right temple bars, said left and right side bars each including a pin extending therefrom for insertion into a corresponding slot disposed in each of said left and right side shields, respectively.

14. A protective eyeglass assembly comprising:
a unitary, decentered lens piece integrally molded from a transparent plastic material, said lens piece including:
  (a) left and right lens panels including a medial edge and a lateral edge, and each having a lens body with a front surface and a rear surface, the front and rear surfaces defining a lens thickness therebetween, the front surface conforming substantially to a portion of the surface of a sphere having a first center, the rear surface conforming substantially to a portion of the surface of a sphere having a second center being offset from one another to taper the lens thickness;
  (b) a central bridge portion connecting said left and right panels; and
  (c) a left side shield and a right side shield extending rearwardly from respective left and right side extremities of said left and right lens panels, said left and right side shields being constructed and arranged to provide protection against peripheral injury to a wearer's eyes, each of said left and right side shields including a slot disposed therein for receiving a corresponding left and right pin extending from respective left and right side bars which are connected to a left and right temple bar, respectively, so as to support the left and right temple bars on said respective left and right side shields;
a support member constructed and arranged to support the lens piece on the wearer and including a left and a right temple bar extending rearwardly from and supported by said left and right side shields; and
wherein the unitary, decentered lens piece is readily removable from the support member such that the lens piece may be easily interchanged with other unitary lens pieces by the wearer.

15. A protective eyeglass assembly comprising:
a unitary, decentered lens piece integrally molded from a transparent plastic material, said lens piece including left and right lens panels each including a medial edge and a lateral edge, and each further having a lens body with a front surface and a rear surface, the front and rear surfaces defining a lens thickness therebetween, the front surface conforming substantially to a portion of the surface of a sphere having a first center, the rear surface conforming substantially to a portion of the surface of a sphere having a second center being offset from one another to taper the lens thickness, said lens piece further including a central bridge portion connecting said left and right panels and a left side shield and a right side shield extending rearwardly from respective left and right side extremities of said left and right lens panels, said left and right side shields being constructed and arranged to provide protection against peripheral injury to a wearer's eyes;
a support member constructed and arranged to support the lens piece on the wearer and including a left and a right temple bar extending rearwardly from and supported by said left and right side shields, the left and right temple bars being hingedly secured to the left and right side shields of said lens piece by a pair of clip members; and
wherein the unitary, decentered lens piece is readily removable from the support member such that the lens piece may be easily interchanged with other unitary lens pieces by the wearer.

16. A protective eyeglass assembly comprising:
a unitary, decentered lens piece integrally molded from a transparent plastic material, said lens piece including:
  (a) left and right lens panels each including a medial edge and a lateral edge, and each further having a lens body with a front surface and a rear surface, the front and rear surfaces defining a lens thickness therebetween, the front surface conforming substantially to a portion of the surface of a sphere having a first center, the rear surface conforming substantially to a portion of the surface of a sphere having a second center being offset from one another to taper the lens thickness (b) a central bridge portion connecting said left and right panels and a left side shield and a right side shield extending rearwardly from respective left and right side extremities of said left and right lens panels, said left and right side shields being constructed and arranged to provide protection against peripheral injury to a wearer's eyes;

(c) left and right upper shields extending between left and right upper extremity portions of said left and right lens panels and said left and right side shields, respectively;

a support member including a frame having left and right lens frame portions connected by a central bridge portion, said left and right lens frames portions each including a lens receiving aperture, said lens piece being received in assembled relation with said frame with said left and right lens panels aligned in registry with said left and right lens frame portions to support the lens piece on the wearer and including a left and a right temple bar extending rearwardly from and supported by said left and right side shields;

means for detachably securing said left and right temple bars to said left and right side shields of said lens piece, said means including a left and a right side bar connected to said respective left and right temple bars, said left and right side bars each including a pin extending therefrom for insertion into a corresponding slot disposed in each of said left and right side shields, respectively; and wherein the unitary, decentered lens piece is readily removable from the support member such that the lens piece may be easily interchanged with other unitary lens pieces by the wearer.

* * * * *